United States Patent [19]
Fritzberg et al.

[11] Patent Number: 5,202,109
[45] Date of Patent: Apr. 13, 1993

[54] CONJUGATES FOR BONE IMAGING AND BONE CANCER THERAPY

[75] Inventors: Alan R. Fritzberg, Edmonds; Jean-Luc E. Vanderheyden, Seattle; Sudhakar Kasina, Kirkland; Jeffrey N. Fitzner, Seattle, all of Wash.

[73] Assignee: NeoRx Corporation, Seattle, Wash.

[21] Appl. No.: 643,578

[22] Filed: Jan. 31, 1991

Related U.S. Application Data

[60] Division of Ser. No. 207,686, Jun. 16, 1988, Pat. No. 5,089,249, which is a continuation-in-part of Ser. No. 205,156, Jun. 10, 1988.

[51] Int. Cl.$^5$ .............................................. A61K 49/02
[52] U.S. Cl. ..................................... 424/1.1; 252/625
[58] Field of Search ........................... 424/1.1; 252/625

[56] References Cited

U.S. PATENT DOCUMENTS

| | | | |
|---|---|---|---|
| 3,852,414 | 12/1974 | Adler et al. ........................... | 424/1.1 |
| 3,974,268 | 8/1976 | Subramanian et al. | |
| 3,987,157 | 10/1976 | Molinski et al. | |
| 3,989,730 | 11/1976 | Subramanian et al. | |
| 4,016,249 | 4/1977 | Adler et al. | |
| 4,017,595 | 4/1977 | Subramanian et al. | |
| 4,032,625 | 6/1977 | Subramanian et al. | |
| 4,082,840 | 4/1978 | Adler et al. | |
| 4,115,541 | 9/1978 | Subramanian et al. | |
| 4,233,284 | 11/1980 | Fawzi | |
| 4,247,534 | 1/1981 | Bevan | |
| 4,337,240 | 6/1982 | Saklad | |
| 4,439,413 | 3/1984 | Hayashi et al. | |
| 4,444,690 | 4/1984 | Fritzberg | |
| 4,504,462 | 3/1985 | Van Duzee et al. | |
| 4,510,125 | 4/1985 | Grogg et al. | |
| 4,560,548 | 12/1985 | Simon et al. ........................... | 424/1.1 |
| 4,582,700 | 4/1986 | Dean et al. | |
| 4,606,907 | 8/1986 | Simon et al. ........................... | 424/1.1 |
| 4,617,184 | 10/1986 | Tsolis et al. | |
| 4,638,051 | 1/1987 | Burns et al. ........................ | 424/1.1 X |
| 4,642,229 | 2/1987 | Cumming et al. | |
| 4,666,698 | 5/1987 | Schwarz | |
| 4,810,486 | 3/1989 | Kelly et al. ........................... | 424/1.1 |
| 4,830,847 | 5/1989 | Benedict et al. | |
| 4,885,153 | 12/1989 | Wilbur et al. | |
| 5,045,303 | 9/1991 | Wilbur et al. | |

FOREIGN PATENT DOCUMENTS

| | | |
|---|---|---|
| 0176288 | 4/1986 | European Pat. Off. |
| 0188256 | 7/1986 | European Pat. Off. |
| 0284071 | 9/1988 | European Pat. Off. |

OTHER PUBLICATIONS

Bodanszky et al., "The Practice of Peptide Synthesis," *Reactivity and Structure Concepts in Organic Chemistry* 21:138–139 (1984).

Eisenhut et al., "$^{131}$I. Labeled Disphosphonates for the Palliative Treatment of Bone Metastases-IV. Syntheses of Benzylidenediphosphonates and Their Organ Distribution in Rats," *Appl. Radiat. Isot.* 38:535–540 (1987).

Ketring, "$^{153}$Sm-EDTMP and $^{186}$Re-HEDP as Bone Therapeutic Radiopharmaceuticals," *Nucl. Med. Biol.* 14:223–232 (1987).

Marsh et al., "Uptake of Technetium-99m Diphosphonate by Metastatic Large Cell Carcinoma of the Lung," *J. Nucl. Med.* 29:726–728 (1988).

*Primary Examiner*—John S. Maples
*Attorney, Agent, or Firm*—Seed and Berry

[57] ABSTRACT

The present invention provides conjugates formed from calcified tissues targeting agents and radiolabeled compounds. One such conjugate comprises a chelate and a targeting agent that is capable of associating with calcified tissue, wherein the chelate contains at least one nitrogen atom or at least one sulfur atom or combinations thereof as the donor atoms.

Another aspect of the invention provides method for using the conjugates for diagnostic and therapeutic purposes, including those related to bone cancer.

5 Claims, 2 Drawing Sheets

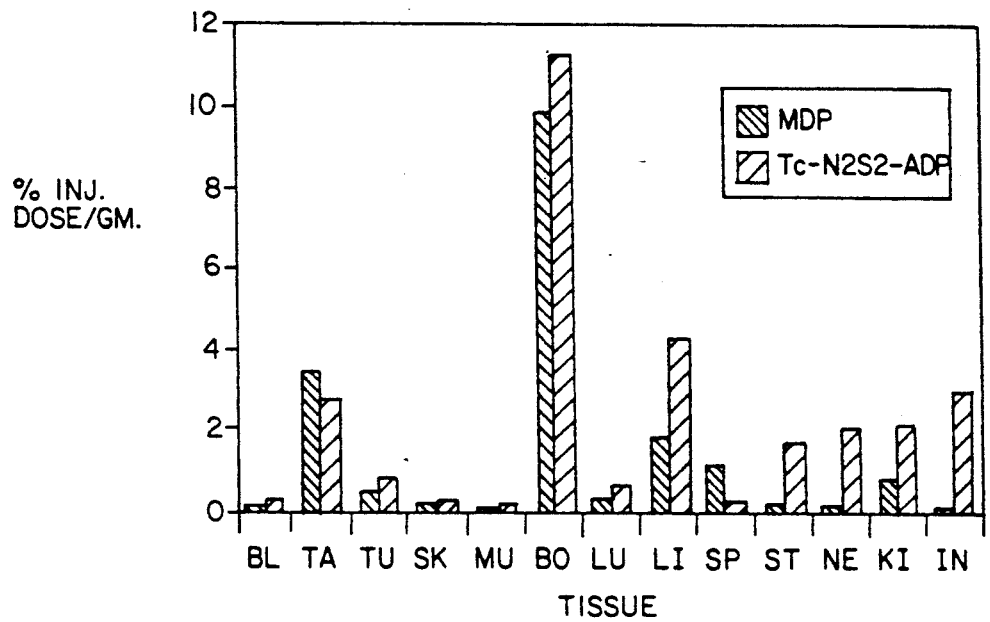
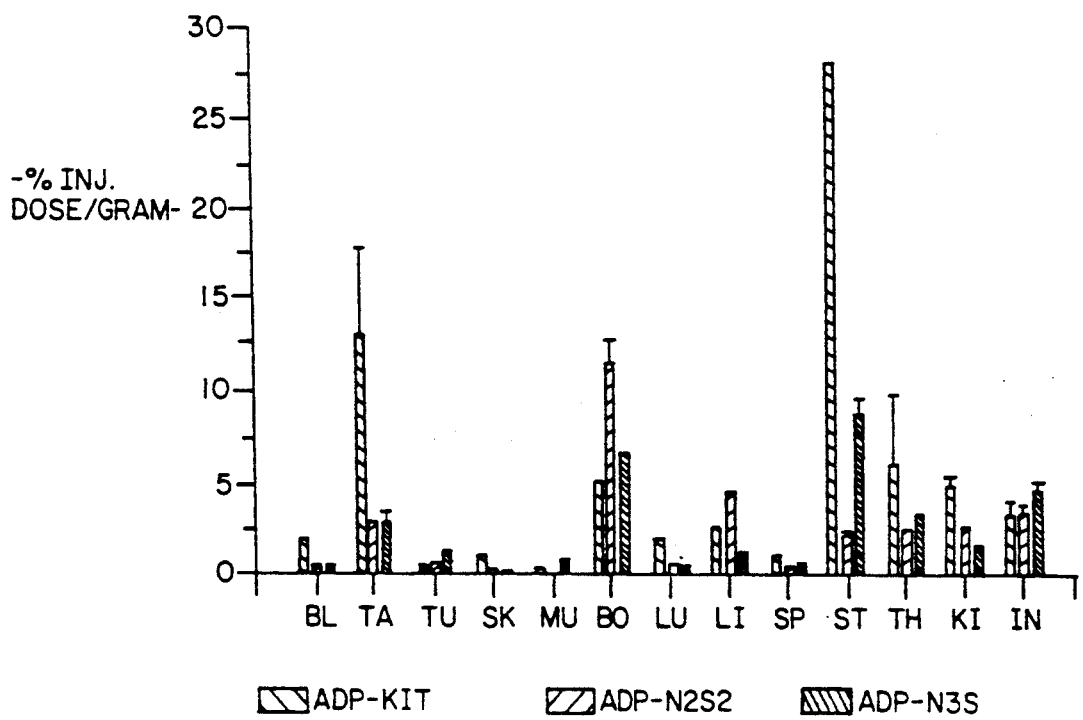

CONJUGATES FOR BONE IMAGING AND BONE CANCER THERAPY

CROSS REFERENCE TO RELATED APPLICATION

This application is a division of Ser. No. 07/207,686, filed Jun. 16, 1988, issued as U.S. Pat. No. 5,089,249 on Feb. 18, 1992, which is a continuation-in-part to Ser. No. 07/205,156, filed Jun. 10, 1988.

TECHNICAL FIELD

The present invention relates generally to conjugates formed from calcified tissue targeting agents and radiolabeled compounds such as chelates, and methods of using these compositions. This invention is more particularly related to conjugates which are useful for bone matrix imaging and bone cancer therapy.

BACKGROUND OF THE INVENTION

The invasive growth of cancer cells into bone tissues often results in severe pain syndromes and may ultimately result in death. Ionizing radiation has been used to achieve a reduction in pain. In particular, external radiation therapy has been applied in cases where bone pain is restricted to focal areas. For disseminated bone metastases, however, a treatment which focuses the radiation dose to bone tissue and particularly to bone metastases is desirable.

Prior to therapy it is necessary to obtain reliable diagnostic information and to this end several approaches have been tried. An approach that has been the subject of a number of patents, for example, U.S. Pat. No. 3,974,268 to Subramanian et al., involves the use of a technetium-99m ($^{99m}Tc$) diphosphonate complex as a skeletal imaging agent. This approach utilizes a diphosphonate as both the bone-seeking agent and the complexing agent for the radionuclide. Such an approach has at least three major disadvantages. First, by involving the bone-seeking agent in the complexation of the metal radionuclide, the ability of the agent to direct, or "target," the radionuclide to the desired site may be diminished. Second, because diphosphonates are known to form polymers, a preparation of diphosphonates and radionuclides typically includes multiple forms of diphosphonate-radionuclide complexes which have differing charge and uptake properties. Third, the complex formed between a diphosphonate and a radionuclide is not of optimal stability which may necessitate purification of the diphosphonate complex prior to use. Further, even a purified diphosphonate complex may lose the radionuclide during its use.

Thus, there is a need in the art for compositions which are capable of both stably binding a radionuclide and preferentially delivering it to calcified tissue. The present invention fulfills this need and further provides other related advantages.

SUMMARY OF THE INVENTION

Briefly stated, the present invention, in one aspect, provides conjugates formed from calcified tissue targeting agents and radiolabeled compounds. One conjugate comprises a chelate and a targeting agent that is capable of associating with calcified tissue, wherein the chelate contains at least one nitrogen atom or at least one sulfur atom or combinations thereof. The chelate may be formed from chelating compounds selected from the group consisting of $N_2S_2$, $N_3S$, $N_2S_3$, $N_2S_4$ and $N_3S_3$ as defined below. Another conjugate comprises a radiolabeled compound and a targeting agent that is capable of associating with calcified tissue, wherein the radiolabeled compound comprises the formula:

$$*X-Ar-R$$

wherein
*X is a radioisotope of iodine, bromine, fluorine, or astatine;
Ar is aromatic or heteroaromatic ring;
R is a chemical bond or a substituent containing 1 to 12 straight-chain carbon atoms that does not activate Ar toward electrophilic substitution on the order produced by hydroxy or amino substitution of the ring, wherein said bond or said substituent has attached thereto a functional group suitable for conjugation.

Another conjugate comprises a radiolabeled compound and a targeting agent that is capable of associating with calcified tissue, wherein the radiolabeled compound is selected from the group consisting of the following formulae:

$$*X\underset{R_1}{\overset{}{>}}C=C\underset{R_2}{\overset{Y}{<}} \quad\quad R_1\underset{R_2}{\overset{}{>}}C=C\underset{Y}{\overset{*X}{<}}$$

wherein *X is a radiohalogen, C=C is a double bonded set of $sp^2$ hybridized carbon atoms, and substituents $R_1$, $R_2$, and Y are as defined below.

In another aspect, the present invention provides kits for producing for radiopharmaceutical use the conjugates described above.

Another aspect of the invention provides methods for using the conjugates described above for diagnostic and therapeutic purposes.

Other aspects of the invention will become evident upon reference to the following detailed description and attached drawings.

BRIEF DESCRIPTION OF THE DRAWINGS

FIG. 1 shows a comparision of $^{99m}Tc$-MDP versus $^{99m}Tc$-$N_2S_2$-ADP.

DETAILED DESCRIPTION OF THE INVENTION

Figure 2B:
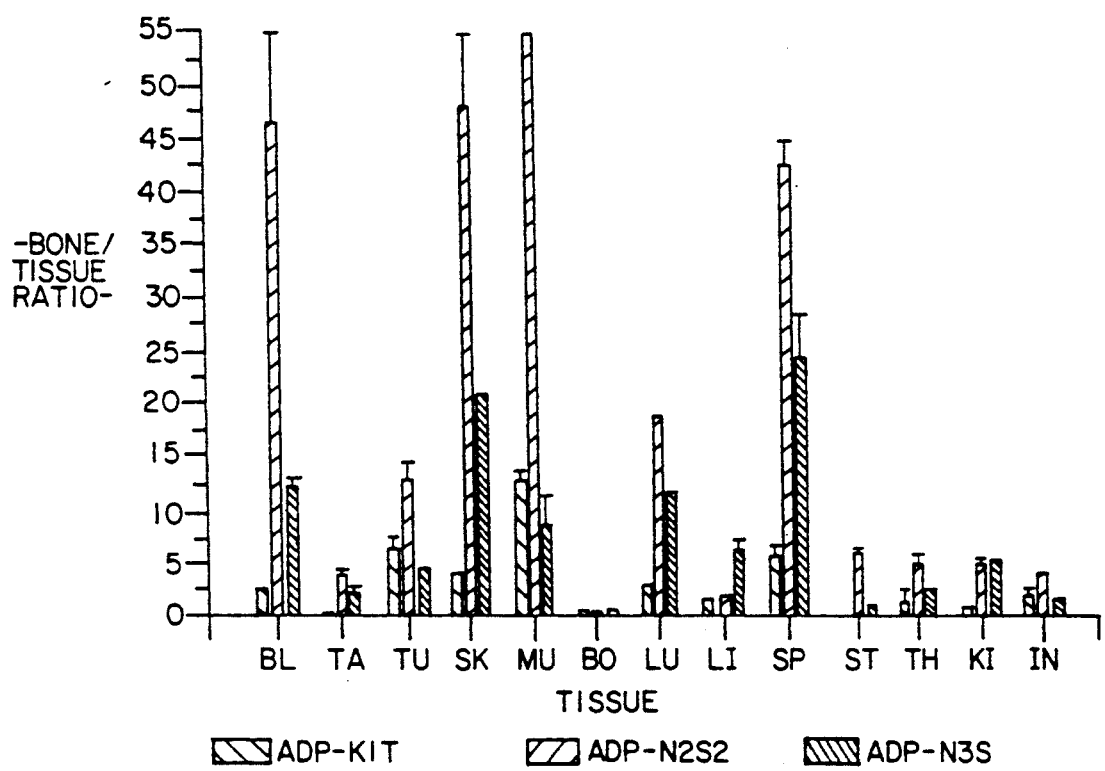
FIG. 2 shows a comparison of $^{99m}Tc$-ADP, $^{99m}Tc$-$N_2S_2$-ADP and $^{99m}Tc$-$N_3S$-ADP.

Prior to setting forth the invention, it may be helpful to an understanding thereof to set forth definitions of certain terms to be used hereinafter.

Calcified tissue—as used herein, includes bone as well as other tissue which may be undergoing pathological calcification.

Targeting agent—is any molecule that has the capacity to associate with calcified tissue.

As noted above, the present invention provides conjugates formed from calcified tissue targeting agents and radiolabeled compounds ("radiolabeled compound-calcified tissue targeting agent conjugates"). Thus, unlike a $^{99m}Tc$-diphosphonate complex for example, the targeting agent in the conjugates is not solely responsible for binding the radionuclide. One advantage of the conjugates is that the radionuclide is afforded greater stability and thus more likely to reach and remain on the target site. In the embodiment in which the radiolabeled compound is a chelating compound, the increased stability and ease of preparation of the congugate is due, in part, to the superior ability of the chelating compound, relative to a diphosphonate for example, to chelate a metal radionuclide. In the embodiment in which the radiolabeled compound is a radiohalogenated compound, the increased stability of the conjugate is due, in part, to the increased electronic stability of the compound and its resistance to enzymatic degradation.

Another advantage of the conjugates of the present invention is that the number of different complexes that may be formed from a single conjugate are limited as opposed to the multiple complexes which are possible when a diphosphonate performs the complexation. Thus, conjugates for diagnosis and therapy may be made in a reproducible manner. Yet another advantage of the conjugates is that the targeting agent by not having to complex the metal radionuclide is unencumbered and therefore more capable of performing its targeting role.

The conjugates of the present invention have the formula:

R—X—T wherein R is a radiolabeled compound, X is a chemical bond or a linking group, and T is a targeting agent. The symbols R, X and T are described in more detail as follows.

T of the formula for the conjugates is a targeting agent. As noted above, a targeting agent has the capacity to associate with calcified tissue. Examples of calcified tissue include bone and other tissues which may be undergoing pathological calcification. The association of a targeting agent with calcified tissue may take a variety of forms including sequestration by the tissue. Targeting agents will be taken up to a greater extent by those areas of the body which are undergoing more active calcification. Examples of targeting agents include phosphorus- containing compounds such as those which contain C—O—P bonds (phosphates), P—O—P bonds, C—C—P bonds (phosphonates), P—C—P bonds (diphosphonates), P—N—P bonds (imidodiphosphonates), or combinations thereof. The targeting agents may be used in a variety of forms, e.g., mono-, di- and polyphosphonates. Examples of phosphonates are those described in U.S. Pat. Nos. 4,233,284 and 4,642,229, as well as derivatives of those compounds. Of the phosphonates, particularly preferred are methylene diphosphonate (MDP) and 4,5-diamino-1-hydroxypentane-1,1-diphosphonate, and 3-amino-1-hydroxypropane-1,1-diphosphonate (ADP).

X of the formula for the conjugates is a chemical bond or a linking group. Illustrative examples of linking groups include: —(CH$_2$)$_n$—, —O—, —(CHOH)$_n$—, —S—, —NH—, —N substituted—, —C(O)—O—, —C(O)—NH—, —C(O)—S—, and combinations thereof.

R of the formula for the conjugates may be (a) a chelate comprising a chelating compound and a metal, or metal oxide, radionuclide, or (b) a radiolabled compound in which the radionuclide is bonded covalently. One conjugate comprises a chelate and a targeting agent that is capable of associating with calcified tissue. The chelate may be formed from chelating compounds that include those containing various combinations of nitrogen and sulfur atoms as the donor atoms for binding a metal or metal oxide. European Patent Application 0188256 published Jul. 23, 1986, publication of grant of patent on Aug. 21, 1991, discloses representative chelating compounds and their synthesis. One example of a chelating compound containing two nitrogens and two sulfurs is referred to herein as "N$_2$S$_2$". Other chelating compounds included within the invention have different numbers of nitrogen and sulfur atoms. Examples of these chelating compounds are identified in like manner herein as "N$_3$S", "N$_2$S$_3$", "N$_2$S$_4$" and "N$_3$S$_3$". Each of these representative chelating compounds is described in more detail below. In addition, the following U.S. patent applications are hereby incorporated in their entirety by reference: U.S. Ser. No. 065,017 (filed Jun. 19, 1987) "Metal Radionuclide Labeled Proteins For Diagnosis And Therapy"; U.S. Ser. No. 172,004 (filed Mar. 23, 1988) "Metal-Radionuclide-Labeled Proteins And Glycoproteins For Diagnosis And Therapy," issued as U.S. Pat. No. 4,965,392 on Oct. 23, 1990; U.S. Ser. No. 201,134 (filed May 31, 1988) "Metal Radionuclide Chelating Compounds For Improved Chelation Kinetics," issued as U.S. Pat. No. 4,988,496 on Jan. 29, 1991; and U.S. Ser. No. 157,284 (filed Feb. 17, 1988) "Anchimeric Radiometal Chelating Compounds."

The N$_2$S$_2$ metal chelating compounds may be dithio, diamino, diamidocarboxylic acids, amino/thio/amido combinations or derivatives thereof, e.g., a N,N'-bis-mercaptoacetyl, (w-x)-diamino carboxylic acid, (x is 1 or 2), esters capable of forming an amide bond in an aqueous medium, and intermediates to the chelate. An example of these compounds has the following formula:

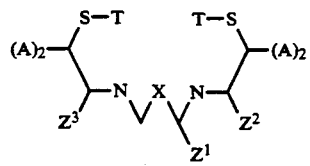

wherein:

one of Z$^1$, Z$^2$, Z$^3$ or Z$^4$ is RCW—(HNV)$_n$Y, and the others are =O or H$_2$;

R is a divalent organic radical of at least 1 carbon atom and typically not more than 10, usually not more than 6 carbon atoms, usually from 1 to 3 carbon atoms having from 0 to 2 heteroatoms which are chalcogen (O, S) or nitrogen and is aliphatic, alicyclic, aromatic or heterocyclic, preferably aliphatic having from 0 to 2, usually 0 to 1 site of aliphatic unsaturation (e.g., ethylenic) and of from 1 to 2 carbon atoms;

W is oxygen or imino (=O or =NH), with the proviso that when Y is —NH$_2$ or NHNH$_2$, the W bonded to the carbon atom bonded to Y is H$_2$;

V is RCW, where the two RCWs may be the same or different, usually being of from 1 to 8, more usually of from 1 to 6 carbon atoms, preferably of from 2 to 3 carbon atoms;

n is 0 or 1;

T is an acyl or acylthio radical of from 2 to 10, usually 2-8 carbon atoms, either a hydrocarbyl acyl or substituted acylradical, usually aryl (e.g., phenyl) or alkyl (e.g., methyl), an organic sulfhydryl radical of from 1 to 10 carbon atoms, either substituted or unsubstituted hydrocarbyl; a heterocycle, particularly a chalcogen (O, S) heterocycle; an acylamidomethylene, where the acyl group is as defined above; hydrogen; sulfonato; an alkali metal ion; or the two T's may be taken together to define a polyvalent metal radionuclide, as the metal ion or metal ion oxide;

Substituents include nitro, cyano, inert halo (aryl or polyhalo), non-oxo-carbonyl (carboxylic acid, amide and ester), and the like;

Y is a chemically reactive moiety and is defined below;

A's are the same or different and are hydrogen, carboxylate or lower alkyl of from 1 to 6 carbon atoms, usually of from 1 to 3 carbon atoms, particularly methyl, usually hydrogen; and X is a bond, methylene or $CHZ^4$;

where T is other than M or H, Y will be other than a targeting agent.

A preferred group of $N_2S_2$ compounds will have one of the following formulas:

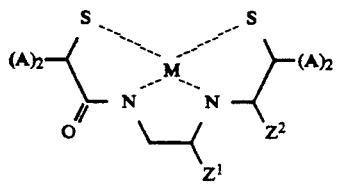

or

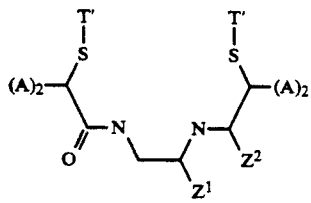

wherein all of the symbols have been defined previously except for M and T', and wherein:

M is a radionuclide capable of being chelated as the metal ion or metal ion oxide; and T' is a sulfur protective group, which includes acyl, acylthio, hydrocarbylthio or substituted-hydrocarbylthio or heterocyclicthio, where the acyl and hydrocarbyl groups may be aliphatic, alicyclic, aromatic or combinations thereof and the acyl group further includes heterocylcic, wherein acyl is normally carboxyacyl; T' will generally be of from 2 to 10 carbon atoms, usually 2 to 8 carbon atoms when acyl, where substituents will include non-oxo-carbonyl (carboxy), halo (aryl), particularly fluoro and chloro, cyano and nitro.

$N_2S_2$ type chelate compounds will for the most part have the following formula:

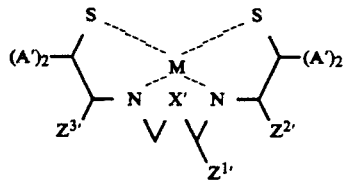

wherein:

one of $Z^{1'}$, $Z^{2'}$, $Z^{3'}$ or $Z^{4'}$ is $R'CW'(HNV')_n\!'Y'$, and the others are =O or $H_2$;

(A')'s are the same or different and are hydrogen, carboxylate or lower alkyl or from 1 to 6, usually 1 to 3 carbon atoms, particularly methyl, usually hydrogen;

n' is 0 or 1;

V' is $R'CW'$, where the (R'CW')'s may be the same or different, usually being of from 1 to 8, more usually of from 1 to 6 carbon atoms, preferably of from 2 to 3 carbon atoms;

W' is oxygen or imino (=N or =O), with the proviso that when Y' is =NH$_2$ or NHNH$_2$, the W' bonded to the carbon atom bonded to Y is $H_2$;

M is a radionuclide capable of being chelated as the metal ion or metal ion oxide;

X' is a bond, methylene or $CHZ^4$;

R' is an aliphatic divalent radical of from 1 to 6, usually from 1 to 3 carbon atoms, having from 0 to 1 site of aliphatic unsaturation and 0 to 2 heteroatoms, usually straight chain and preferably methylene or polymethylene of from 2 to 3 carbon atoms; and Y' is a chemically reactive moiety as defined below.

The dashed lines in the formulae presented for the chelate compounds of the invention represent four coordinate covalent bonds between the metal radionuclide M and each of the two sulfur and the two nitrogen atoms shown in the formulae. Thus, the metal radionuclide is bound through relatively stable bonds in the chelate compounds of the invention.

An example of a $N_2S_2$ conjugate has the formula:

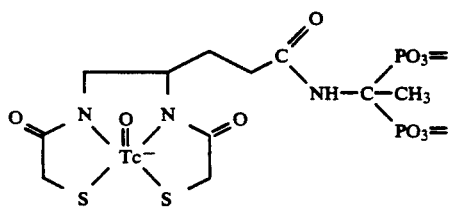

The $N_3S$ metal chelating compounds will have, for the most part, the following formula:

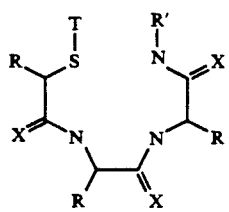

wherein:

T is H or a sulfur protecting group;

each X independently represents $H_2$ or O;

each R independently represents a substituent selected from the group consisting of hydrogen; alkyl; carboxylate; sulfonate; geminal dialkyl; a non-alkyl side chain of an amino acid other than cysteine (alkyl side chains being covered when R is an alkyl group); and —(CH$_2$)$_n$—Z;

Z represents a chemically reactive moiety;

n is an integer of from 1 to about 4; and

R' is $H_2$; —(CH$_2$)$_n$—Z; or an alkyl group having one or more polar groups substituted thereon;

wherein the compound comprises at least one —(CH$_2$)$_n$—Z substituent.

When Z is —NH$_2$, n should be at least 2. When Z is other than —COOH, n preferably is 3.

The sulfur protecting group may be selected from alkyl, aryl, acyl (preferably alkanoyl or benzoyl), thioacyl groups having 1 to about 7 carbons, and organothio groups having 1 to about 10 carbons.

For the R groups, the alkyl groups generally contain from 1 to 7 carbons, preferably from 1 to 4 carbons, and most preferably represent methyl.

An example of a N₃S conjugate has the formula:

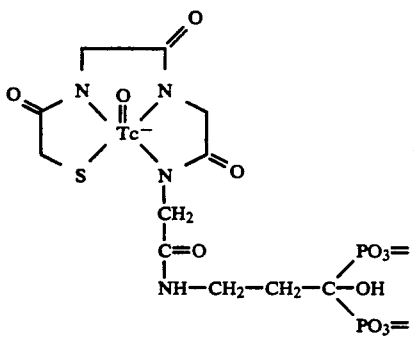

The N₂S₃ and N₂S₄ chelating compounds have the following formula:

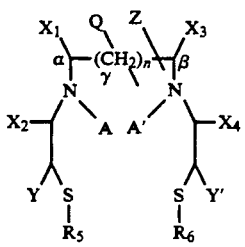

Examples of specific embodiments of the elements include the following.

$X_1$ and $X_2$ may be H or an oxy group (=O), but both are not =O. Likewise, $X_3$ and $X_4$ may be H or =O, but both are not =O. By selecting =O for $X_1$ or $X_2$, the N interposed between the carbons to which $X_1$ and $X_2$ are bonded will be an amide. Likewise, by selecting =O for $X_3$ or $X_4$, the N interposed between the carbons to which $X_3$ and $X_4$ are bonded will be an amide. Thus, a compound with zero, one or two amides may be formed by the appropriate selection of $X_1$, $X_2$, $X_3$ and $X_4$. Amide nitrogens, relative to amine nitrogens, afford greater stability to the complex formed with a metal, but at the expense of a diminished acceleration of complex formation. Thus, by selection of $X_1$, $X_2$, $X_3$ and $X_4$, compounds with a wide variety of chelating properties may be formed.

A is a hydrogen (H), alkyl group of C₆ or less, —CH₂—CH₂—S—R₁ or —CO—CH₂—S—R₁, except when either $X_1$ or $X_2$ is =O, A is H. Similarly, A' is H, alkyl group of C₆ or less, —CH₂—CH₂—S—R₂ or —CO—CH₂—S—R₂, except when either $X_3$ or $X_4$ is =O, A' is H. Y is —CH₂—S—R₃, or H, when A is H or an alkyl group of C₆ or less and A' is H or an alkyl group of C₆ or less. Alternatively, when either A or A' or both are not H or an alkyl group of C₆ or less, then Y is H. Similarly, Y' is —CH₂—S—R₄, or H, when A is H or an alkyl group of C₆ or less and A' is H or an alkyl group of C₆ or less. However, Y and Y' are both not H when A is H or an alkyl group of C₆ or less and A' is H or an alkyl group of C₆ or less. Alternatively, when either A or A' or both are not H or an alkyl group of C₆ or less, then Y is H. Similarly, Y' is —CH₂—S—R₄, or H, when A is H or an alkyl group of C₆ or less and A' is H or an alkyl group of C₆ or less. However, Y and Y' are both not H when A is H or an alkyl group of C₆ or less and A' is H or an alkyl group of C₆ or less. Alternatively, when either A or A' or both are not H or an alkyl group of C₆ or less, then Y' is H. Thus, compounds of the formula depicted above may be formed containing two nitrogens and three or four sulfurs ("N₂S₃" and "N₂S₄", respectively). For "N₂S₄" compounds, two of the sulfurs are the sulfurs bearing R₅ and R₆ and the remaining two sulfurs are from A and A' or Y and Y'. The following formulae depict examples of N₂S₄ compounds in which two sulfurs are from Y and Y' (A) or in which two sulfurs are from A and A' (B).

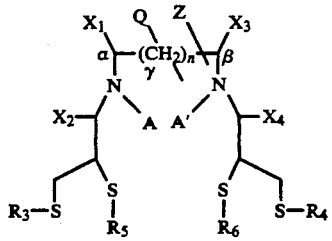

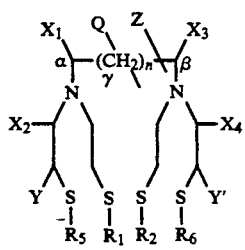

$R_1$, $R_2$, $R_3$, $R_4$, $R_5$ and $R_6$ are independently selected from sulfur protecting groups. Groups which may be used include any of the alkyl, acyl and aryl groups, disulfides and bunte salts known by those skilled in the art. Preferred groups are those that result in the formation of a thioacetal, hemithioacetal, thioester or acetamidomethyl substituent. Particularly preferred groups include p-anisylidine, acetonyl, tetrahydrylfuranyl, ethoxyethyl, tetrahydrylpyranyl, acetamidomethyl and derivatives thereof. When conjugated to a targeting agent, the protecting groups may be removed and left as sulfydryls either during storage or just prior to radiolabeling.

Q may be H or a polar group. One function of a polar group is to increase the hydrophilicity of the compound, e.g., in order to increase its aqueous solubility. Groups which may be used include carboxylates, sulfonates and secondary alcohols. A preferred group is —CH₂—COOH. Q may be attached to one of the positions designated as α, β, and γ. Because the number of methylene carbons at the γ position is defined by n which may be greater than one, the γ position includes additional points for attachment of Q.

The distance by which the nitrogen atoms are separated may be increased by interposing methylene (—CH₂—) groups between the carbons bonded to the nitrogens. When the number of —CH₂— groups, represented by n, is greater than zero, then the number of carbon atoms separating the nitrogen atoms in compound I is increased accordingly. Preferred integers for n are 0 to 2.

Z is —(W)$_m$—R'. W is a group that functions as a "spacer arm" and may be useful to distance R' from the chelating portion of the compound. Groups which may be used include methylene (—CH₂—), methyleneoxy (—CH$_2$—O—), methylenecarbonyl (—CH$_2$—CO—), or combinations thereof. The number, m, of groups such as these would be typically 0 to 30 and preferably 0 to 5.

Z, or R' when m is 0, may be attached to one of the positions designated as $\alpha$, $\beta$, and $\gamma$. Because the number of methylene carbons at the $\gamma$ position is defined by n which may be greater than one, the $\gamma$ position includes additional points for attachment of a Z or an R'.

R' is a chemically reactive moiety. The moiety may be strongly electrophilic or nucleophilic and thereby be available for reacting directly with a targeting agent. Alternatively, the moiety may be a weaker electrophile or nucleophile and therefore require activation prior to the conjugation with a targeting agent. This alternative would be desirable where it is necessary to delay activation of R' until a compound has been formed. In either scenario R' is chemically reactive, the scenarios differ by whether following formation of a compound, R' is reacted directly with a targeting agent or is reacted first with one or more chemicals to render R' capable of reacting with a targeting agent. A discussion of reactions illustrative of a direct reaction with R' and of activation of R' is found below.

N$_3$S$_3$ compounds which contain three nitrogens and three sulfurs, have the following formula:

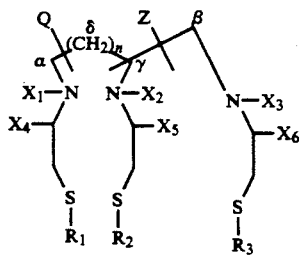

Examples of specific embodiments of the elements include the following.

R$_1$, R$_2$, and R$_3$ are independently selected from sulfur protecting groups. Groups which may be used include any of the alkyl, acyl, aryl groups, disulfides and bunte salts known by those skilled in the art. Preferred groups are those that result in an acyl, a thioacetal or a hemithioacetal. Particularly preferred groups include thioesters, p-anisylidine, acetonyl, tetrahydrylfuranyl, ethoxyethyl, tetrahydrylpyranyl, acetamidomethyl, and derivatives thereof.

X$_1$ and X$_2$ are independently selected from hydrogen (H) and an alkyl group of C$_6$ or less. X$_3$ is an H, an alkyl group of C$_6$ or less, or Z. X$_4$, X$_5$, and X$_6$ are independently selected from H and =O. The selection of =O results in the presence of an amide. Thus, a compound with zero, one, two or three amides may be formed by the appropriate selection of X$_4$, X$_5$, and X$_6$. Amide nitrogens, relative to amine nitrogens, afford greater stability to the complex formed with a metal, but at the expense of a diminished acceleration of complex formation. Thus, by selection of X$_4$, X$_5$, and X$_6$, compounds with a wide variety of chelating properties may be formed.

Q may be H or a polar group. One function of a polar group is to increase the hydrophilicity of the compound, e.g., in order to increase its aqueous solubility. Groups which may be used include carboxylates, sulfonates and secondary alcohols. A preferred group is —CH$_2$—COOH. Q may be attached to one of the positions designated as $\alpha$, $\beta$, $\gamma$ and $\delta$. Because the number of methylene carbons at the $\delta$ position is defined by n which may be greater than one, the $\delta$ position includes additional points for attachment of Q.

The distance by which nitrogen atoms are separated may be increased by interposing methylene (—CH$_2$—) groups between the carbons bonded to the nitrogens. When the number of —CH$_2$— groups, represented by n, is greater than zero, then the number of carbon atoms separating the nitrogen atoms in compound II is increased accordingly. Preferred integers for n are 0 to 4.

Z is —(W)$_m$—R'. W is a group that functions as a "spacer arm" and may be useful to distance R' from the chelating portion of the compound. Groups which may be used include methylene (—CH$_2$—), methyleneoxy (—CH$_2$—O—), methylenecarbonyl (—CH$_2$—CO—), or combinations thereof. The number, m, of groups such as these would be typically 0 to 30 and preferrably 0 to 5.

Z, or R' when m is 0, may be attached to X$_3$ or to one of the positions designated as $\alpha$, $\beta$, $\gamma$, and $\delta$. Because the number of methylene carbons at the $\delta$ position is defined by n which may be greater than one, the $\delta$ position includes additional points for attachment of a Z or an R'.

R' is a chemically reactive group and the discussion of it is found below.

The N$_3$S$_3$ compound formula, the carbon designated as $\beta$ may be bonded to any one of the carbons designated as $\alpha$, $\gamma$ and $\delta$. The following formulee depict compounds in which the $\beta$ carbon is bonded to the $\gamma$ carbon (A) and the $\beta$ carbon is bonded to the $\delta$ carbon (B).

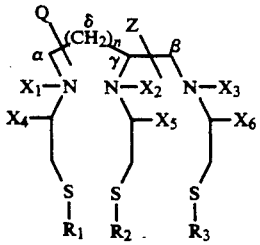

A

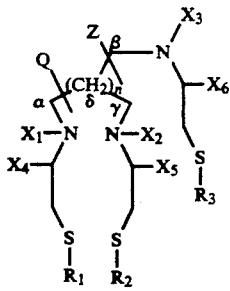

B

Preferred metals and metal oxides for any of the chelating compounds described above are those that are radionuclides. Particularly preferred are $^{64}$Cu, $^{67}$Cu, $^{97}$Ru, $^{99m}$Tc, $^{105}$Rh, $^{109}$Pd, $^{186}$Re, $^{188}$Re, $^{198}$Au, $^{199}$Au, $^{203}$Pb, $^{212}$Pb, and $^{212}$Bi.

Another conjugate comprises a radiolabeled compound and a targeting agent that is capable of associating with calcified tissue, wherein the radiolabeled compound comprises the formula:

*X—Ar—R wherein

*X is a radioisotope of iodine, bromine, fluorine, or astatine;

Ar is aromatic or heteroaromatic ring;

R is a chemical bond or a substituent containing 1 to 12 straight-chain carbon atoms that does not activate Ar toward electrophilic substitution on the order produced by hydroxy or amino substitution of the ring, wherein said bond or said substituent has attached thereto a functional group suitable for conjugation.

As utilized herein, the symbol *X indicates any radioisotope of: iodine, particularly I-123, I-125, and I-131; bromine, particularly Br-75, Br-76 and Br-77; fluorine, particularly F-18; and, astatine, particularly At-211. Preferred radiohalogens *X for diagnostic imaging purposes include I-131 and most preferably I-123 for imaging with gamma cameras; and for positron tomographic imaging: F-18, Br-75, and Br-76. For clinical radiotherapy, preferred radiohalogens *X include I-131, Br-77, and At-211. Preferred radiohalogens *X for in vitro radioimmunoassay purposes include I-125, and I-131. Pursuant to this invention the radiohalogen *X is preferably para- or meta-positioned on ring Ar relative to substituent R in order to render the radiohalogen less susceptible to catabolism by dehalogenase enzymes.

The symbol Ar indicates any aromatic or heteroaromatic ring. Preferred rings Ar include benzene, pyridine, furan, and thiophene, the latter three because of the enhanced water solubility they convey. The attachment of the radiohalogen to a carbon atom in an aromatic ring is preferred over attachment to an alkyl carbon atom due to the increased bond strength of the carbon-halogen bond in the aromatic ring. The nature of the aromatic ring is not critical and may be mono-, bi-, tri-, or higher number of rings, but the monocyclic ring is preferred based on increased water solubility. The aromatic rings may consist of all carbon atoms or may contain heteroatoms such as nitrogen, oxygen, or sulfur. Inclusion of heteroaromatic rings such as pyridines, furans, or thiophenes can assist in increasing water solubilities of the radioiodinated small molecule conjugates. Further substitution on the aromatic ring, exclusive of *X and R, with polar substituents such as a nitro, sulfonic acid, carboxylic acid, or dialkyl amino group can also be used to enhance water solubility. Increased water solubility is desirable to give higher yields and less potential aggregation in the conjugation reaction with targeting agent and to cause less perturbation of the lipophilicity of the antibody conjugate. Other substituents can be added to impart some control against enzymatic degradation.

The symbol R indicates any substituent that meets the following three requirements: First, the R substituent must not highly activate ring Ar toward electrophilic substitution. In other words, R cannot be linked to ring Ar by a linkage that increases the electron density of Ar on the order of the increase produced by a hydroxy or amino substitution. Second, R should be a short-chain substituent so that unconjugated or cleaved radiohalogenated molecules can be rapidly removed by the kidneys. Thus, R may contain an alkyl or other spacer chain between the aryl linkage and the functional group for targeting agent conjugation, but such a spacer chain should preferably contain no more than 5, and most preferably no more than 3, straight-chain carbon atoms. Third, the R substituent should bear a functional group that is available for conjugation to targeting agent under conjugation conditions, such as acylation or amidination, that preserve the biological activity of the targeting agent. Thus, R should provide a functional group, such as imide ester or imidate ester, for covalent attachment of corresponding functional groups (or conjugated attachment sites) of targeting agents, or carrier molecules such as amino acid polymers that can in turn be conjugated to targeting agent molecules.

Suitable functional groups for the above-stated purpose include phenolic esters (e.g., para-nitrophenol), imide esters (e.g., succinimide ester), imidate esters, anhydrides, acylsuccinimides, aldehydes, isothiocyanates, diazo, amines, hydrazines, alkyl halides, maleimides, and other groups that can be used to attach the molecule to a targeting agent through a covalent bond.

Representative R substituents include alkyl acids, amido alkyl acid, nitrile, alkyl nitriles, amido alkyl nitride, imide ester, alkyl imide esters, amido alkyl imide ester, imidate ester, alkyl imidate esters, and amido alkyl imidate ester.

Illustrative but nonlimiting examples of radiohalogenated small molecules of this invention include: N-succinimidyl-3-(4-[131I]iodophenyl)propionate; methyl-3-(4-[131I]iodophenyl)propioimidate; N-succinimidyl-4-[131I]iodobenzoate; methyl-4-[131I]iodobenzimidate; N-succinimidyl-4-[131I]iodobenzamido-acetate or N-succinimidyl-4-[131I]iodohippurate; methyl-4-[131I]iodobenzamiodoacetimidate; and 4-[131I]iodobenzamidoacetonitrile. The synthesis of radiohalogenated small molecules such as these is described in European Patent Application 0 203 764 published Dec. 3, 1986. The radiolabeling procedures described therein generally involve substituting an organometallic group which is a tri-alkyl stannane of the formula Sn(R)3 wherein R is a lower alkyl group, preferably Sn(n-Bu)3 or SnMe3, on a haloaromatic compound. A radioisotope of a halogen then is substituted for the organometallic group by halodemetalization. In addition, U.S. Ser. No. 852,740 (filed on Apr. 21, 1986), entitled "Radiohalogenated Small Molecules For Protein Labeling," abandoned in favor of U.S. Ser. No. 338,497 (filed on Apr. 13, 1989), issued as U.S. Pat. No. 4,885,153 on Dec. 5, 1989, is hereby incorporated in its entirety by reference.

Another conjugate comprises a radiolabeled compound and a targeting agent that is capable of associating with calcified tissue, wherein the radiolabeled compound is selected from the group consisting of the following formulae:

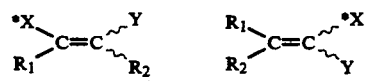

wherein *X is a radiohalogen, C=C is a double bonded set of sp2 hybridized carbon atoms, and substituents R1, R2, and Y are as defined below.

R1 and R2 are substituents independently selected from among hydrogen; alkyl or substituted alkyl, provided that any sp2 or sp carbon atom substituted on the alkyl is separated from C=C by at least one fully substituted sp3 carbon atom; aryl or substituted aryl, provided, first, that the aryl is bonded directly to C=C and, second, that when the aryl is substituted ortho or para relative to C=C the substituent does not donate electrons to the aryl via resonance; heteroalkyl, provided, first, that no heteroatom of the heteroalkyl bonds directly to C=C and, second, that any sp2 or sp hybridized carbon bonded to a heteroatom of the heteroalkyl is not bonded directly to or otherwise conjugated with C=C and, third, that where a single sp$^3$ carbon intervenes between C=C and an sp$^2$ or sp carbon bonded to a heteroatom that intervening sp$^3$ carbon must be fully substituted; heteroaryl, provided that a heteroatom of the heteroaryl is not bonded directly with C=C; mixed alkylaryl, provided, first, that no heteroatom is bonded to C=C and, second, that either an aryl moiety of the mixed alkylaryl is directly bonded to C=C or that any aryl moiety is separated from C=C by at least one sp$^3$ carbon atom and, where only one sp$^3$ hybridized carbon atom intervenes between C=C and an aryl moiety, that intervening sp$^3$ carbon must be fully substituted. By fully substituted sp$^3$ carbon atom as used herein is meant a carbon atom not substituted with hydrogen or any substituent such that isomerization of C=C can take place.

Y is a substituent containing any of the groups described above for $R_1$ and $R_2$, except that Y cannot be hydrogen, and bearing a functional group suitable for binding to targeting agent under conditions that preserve the biological activity of the targeting agent.

As utilized herein, the symbol "*X" indicates any radioisotope of: iodine, particularly $^{123}$I, $^{125}$I, and $^{131}$I; bromine, particularly $^{75}$Br, $^{76}$Br, and $^{77}$Br; fluorine, particularly $^{18}$F; and, astatine, particularly $^{211}$At. Preferred radiohalogens *X for diagnostic imaging purposes include $^{131}$I and most preferably $^{123}$I for imaging with gamma cameras, and $^{18}$F, $^{75}$Br, $^{76}$Br, and $^{124}$I for positron tomographic imaging. For clinical radiotherapy, preferred radiohalogens *X include $^{131}$I, $^{77}$Br, and $^{211}$At.

Symbol "C=C" indicates a double bonded set of sp$^2$ hybridized carbon atoms known as an alkene. Each of the doubly bonded carbons has two additional sp$^2$ orbitals available for bonding. Radiohalogen *X bonds to one of these sp$^2$ orbitals. The symbols "$R_1$" and "$R_2$" refer to two additional vinyl substituents of the alkene, that is, to atoms or groups that are bonded to another two of the four available sp$^2$ orbitals. Substituent Y bonds to the fourth sp$^2$ orbital of C=C.

It is essential that substituents $R_1$ and $R_2$ (and also Y) do not destabilize the radiohalogen-sp$^2$ carbon bond. For example, directly bonding a heteroatom such as oxygen or nitrogen to either of the sp$^2$ hybridized carbon atoms of C=C may change the electron character of the alkene, resulting in loss of the radiohalogen. Some heteroatoms may be suitable for bonding directly to group C=C provided that the heteroatom does not donate nonbonding electrons to C=C. Examples of such heteroatoms include nitrogen, when bonded to another functional group such as carbonyl, that will delocalize the nonbonding electrons, e.g., a nitrogen in an amide bond. Thus, the substituents $R_1$ and $R_2$ may be heteroalkyl or heteroaryl groups, but it is preferred that a heteroatom is not directly bonded to group C=C. It is also particularly important that vinyl substituents $R_1$ and $R_2$ do not render the alkene susceptible to nucleophilic addition. Examples of such nucleophilic addition to C=C include additions to $\alpha,\beta$-unsaturated carbonyl compounds in reactions known as Michael-type additions, as defined in March, J., *Advanced Organic Chemistry*, 3rd Edition, John Wiley & Sons, New York, NY 664-666, 1985, which is hereby incorporated by reference. Thus, for heteroalkyl groups, any sp$^2$ or sp carbon bonded to a heteroatom must not be bonded directly to or otherwise conjugated with C=C. Furthermore, where a single sp$^3$ hybridized carbon atom intervenes between C=C and an sp$^2$ or sp carbon that is bonded to a heteroatom, that sp$^3$ carbon must be fully substituted so that an isomerization of the C=C double bond is not possible. Otherwise, protons bonded to a sp$^3$ carbon atom $\alpha$ to the heteroatom and allylic to group C=C would be acidic, leading to activation of group C=C and migration of that double bond, which would produce the highly undesirable allylic radiohalogenated small molecule.

It is also important that $R_1$ and $R_2$ be inert toward biological molecules under physiological conditions. For example, reducing sugars would not be suitable $R_1$ and $R_2$ substituents, because such noninert substituents might lead to nonspecific glycosylation and radiolabeling of nontargeted tissues in vivo.

Permissible alkyl substituents $R_1$ and $R_2$ include protons and branched, straight-chain, or cyclic alkyl groups containing from 1 to about 12 carbon atoms that are preferably substituted with protons or methyl groups. Most preferably, $R_1$ and $R_2$ are individually selected from among protons and methyl groups. Permissible heteroalkyl substituents $R_1$ or $R_2$ include, but are not limited to, those in which the alkyl moiety either is substituted with substituents from the group halogen, OH, OG, $O_2$CG, $CO_2$G, $CONH_2$, CONG, CONHG, $NH_2$, $NG_2$, NHG, SH, SR, SOG, $SO_2$G, $SO_2NG_2$, $SO_2NH_2$, and $SO_2NHG$ or which contain as linking groups —O—, —NH—, —NG—, —CO—, —$CO_2$—, —CONH—, —CONG—, —S—, —SO—, —$SO_2$—, —$CO_2$NH—, and —$SO_2$NG—, wherein G is selected from alkyl of from 1 to about 8 carbon atoms, alkenyl of from 1 to about 8 carbons, aryl.

Permissible aryl substituents $R_1$ and $R_2$ include, but are not limited to, 5, 6, and 7 carbon aromatic rings, with the most preferable aryl substituent being phenyl. Permissible polynucleararyl substituents $R_1$ and $R_2$ include those having up to 3 aryl rings, with each ring containing 5, 6, or 7 carbon atoms. Permissible heteroaryl substituents $R_1$ and $R_2$ include, but are not limited to, 5, 6, and 7 member rings containing from 1 to about 3 heteroatoms selected from O, S, and N, with the most preferable heteroaryl substituent being pyridine. The foregoing aryl, polynucleararyl, and heteroaryl groups may be substituted with as many as 3 ionizable groups, such as nitro, sulfonic acid, carboxylic acid, and amino in order to aid in the solubilization in aqueous solutions. The aryl, polynucleararyl, and heteroaryl substituents $R_1$ and $R_2$ may also be substituted with alkyl and with heteroalkyl groups containing heteroatom such as oxygen, nitrogen, and sulfur. In addition, U.S. Ser. No. 171,731 (filed Apr. 5, 1988), entitled "Vinyl Substituted Radiohalogen Conjugates For Protein Labeling," issued as U.S. Pat. No. 4,876,081 on Oct. 24, 1989, is hereby incorporated in its entirety by reference.

Three methods are provided for producing the conjugates described herein. The two methods for producing a conjugate from a fully formed compound suitable for radiolabeling have a different order for the addition of the targeting agent. In the first method the targeting agent is joined to a radiolabeled compound, e.g., after a metal or metal oxide has been added to a chelating compound. Conversely, in the second method the targeting agent is joined to a fully formed but unlabeled compound, e.g., before a metal or metal oxide has been added. In both methods, however, a conjugate has a targeting agent joined via a "chemically reactive moiety" (also herein called a "functional group suitable for conjugation"). As noted above, a targeting agent may be joined by a direct reaction with a chemically reactive moiety or following the activation of a chemically reactive moiety.

The step of combining a targeting agent with a labeled or unlabeled compound may be performed by direct reaction of the targeting agent with a chemically reactive moiety. Alternatively, it may be desirable to include a preparatory step before the step of combining. For example, a targeting agent may be modified in preparation for a direct reaction with a chemically reactive moiety. The modification of a targeting agent includes reaction with any of the numerous bifunctional reagents reported in the literature.

A direct reaction with a chemically reactive moiety by modified or unmodified targeting agent is intended to mean that a chemically reactive moiety is capable of reacting with the modified or unmodified targeting agent. For example, a chemically reactive moiety may be an alkyl group containing a good leaving group, e.g., a halide, or a carbonyl-containing group, such as an anhydride, acid halide, or "active ester." The term "active ester" is known to refer to esters which are highly reactive in nucleophilic substitution reactions. In the present invention, the modified or unmodified targeting agent would be the nucleophile. Typically the esters will be activated phenols and cyclic compounds based on hydroxylamine. Examples of commonly use ester groups are tetrafluorophenyl, N-hydroxysuccinimidyl, nitrophenyl, isothiocyanate and substituted isothiocyanates. Alternatively, a chemically reactive moiety may be a nucleophilic group, such as an amino or sulfhydryl group, which is capable of reacting with a modified targeting agent, e.g., containing a maleimide group.

Another way to perform a step in preparation for the step of combining a targeting agent and a labeled or unlabeled compound is to convert a chemically reactive moiety to a form capable of reacting with the targeting agent. Examples of conversions of a chemically reactive moiety include where a chemically reactive moiety is a carboxyl group and is then activated. Activation of a carboxyl group includes formation of an "active ester" as defined above. Another example of a conversion is where a chemically reactive moiety is a succinimide derivative containing a protective group, such as phenylsulfonyl. Upon removal of the group, the succinimide is converted to a maleimide which is highly reactive in nucleophilic addition reactions. Alternatively, a chemically reactive moiety may be a nucleophilic group, such as an amino or sulfhydryl group, and the conversion comprises reaction with a bifunctional reagent. It will be evident to one skilled in the art that a variety of bifunctional reagents, both homobifunctional and heterobifunctional, may be employed within the present invention.

A third method for providing a conjugate is to incorporate a targeting agent into a compound, which is suitable for radiolabeling, as the compound is being synthesized. In other words, a targeting agent is covalently attached to a precursor of a compound suitable for radiolabeling. An example of such a compound is a precursor of one of the chelating compounds described above. Following attachment of a targeting agent to a precursor of a compound, the synthesis of the compound is completed so that it will be suitable for radiolabeling.

The above-described chelating compounds are radiolabeled with an appropriate radionuclide to produce the corresponding chelate. The radiolabeling step may be done either before or after the compound is attached to the targeting agent. Conventional procedures are used for radiolabeling the chelating compounds. For example, pertechnetate ($^{99m}TcO_4$-) or perrhenate ($^{186}$ or $^{188}ReO_4$-) are generally contacted with a chelating compound in the presence of a reducing agent to effect reduction of the radionuclide to an oxidation state at which chelation can occur. Many suitable reducing agents are known, including but not limited to stannous ion, (e.g., in the form of stannous salts such as stannous chloride or stannous fluoride), metallic tin, dithionite, formamidine sulfinic acid, ferrous ion (e.g., in the form of ferrous salts such as ferrous chloride, ferrous sulfate, or ferrous ascorbate), and alkali salts of borohydride. Preferred reducing agents are stannous salts.

Alternatively, the pertechnetate or perrhenate may be reduced in the presence of a relatively labile complexing agent such as gluconic acid or citric acid to form intermediate exchange complexes ($^{99m}Tc$-gluconate or $^{186}Re$-citrate). When the exchange complexes are contacted with the chelating compound under appropriate reaction conditions, the radionuclide metal is transferred to the chelating compound, thereby producing a radionuclide metal chelate.

The formation of intermediate exchange complexes is desirable for the radiolabeling of a number of chelating compounds with certain radionuclides. Improved yields of the radiolabeled chelate may be achieved through the use of complexing agents, compared to the yields resulting from reaction of chelating compounds alone with a radionuclide.

The exchange complex may serve to stabilize the radionuclide. For example, certain radionuclides are available in oxidation states at which chelation by the above-described chelating compounds does not occur. Reducing agents are used to effect reduction of the radionuclide to an oxidation state at which chelation can occur, as described for $^{99m}Tc$ and $^{188}$ or $^{186}Re$ above. Contacting the radionuclide with a reducing agent in the presence of a complexing agent to form an exchange complex serves to stabilize the reduced radionuclide thereby minimizing reoxidation thereof. Exchange complexes may be used to minimize reoxidation of such "redox active" radionuclides as radioisotopes of Tc, Re, Ru, Rh, Fe, Co, Cr, V, Sn, and Os, among others.

Exchange complexes also may be used to stabilize certain radionuclides so that polymerization thereof (e.g., formation of hydrous oxides) is minimized. Radionuclides that are susceptible to polymerization include, but are not limited to, radioisotopes of W, Mo, Ni, and Nb.

The exchange complexes often have a faster rate of formation (i.e., faster kinetics of complex formation), but a lower stability with respect to radionuclide binding than the radionuclide metal chelate compounds. Thus, the complexing agent binds the radionuclide much more quickly than does the chelating compound. The rapid formation of the exchange complex stabilizes the radionuclide, whereas the radionuclide would remain unbound longer (providing more opportunity for reoxidation or polymerization) if contacted with the chelating compound alone.

Radionuclides may be reacted with complexing agents at a wide range of temperatures to form exchange complexes (e.g., from 0° C. to 100° C., preferably from room temperature to about 37° C.). For convenience, the reaction is generally conducted at room temperature (about 18° C.–25° C.) for many complexing agents. Due to the fast kinetics of complex formation, reaction for less than one hour, preferably about 10 minutes, is sufficient for exchange complex formation with most complexing agents.

Since exchange complexes are less stable (e.g., less thermodynamically stable) than the final chelate compound with respect to radionuclide binding, contacting the exchange complex with the chelating compound may result in transfer of the radionuclide to the chelating compound. Heating is often required to promote transfer of the radionuclide. A radionuclide may be reacted with a reducing agent in the presence of a complexing agent to form an exchange complex. The chelating compound then is added to the reaction mixture, followed by heating to promote transfer of the radionuclide. Alternatively, the radionuclide, reducing agent, complexing agent, and chelating compound all may be added to a single reaction mixture and heated together to form the final chelate. The improved yields of the radionuclide chelate that result when a complexing agent is used demonstrate that the complexing agents facilitate formation of the chelate.

Lyophilized preparations comprising two or more reagents may be used in the radiolabeling reactions. For example, a reducing agent and complexing agent may be combined in an aqueous solution and then lyophilized. Optionally, one or more stabilizer compounds may be added prior to lyophilization. Many such stabilizer compounds are known. See, for example, U.S. Pat. Nos. 4,440,738 and 4,510,125. Advantageously, gentisic acid is added to stabilize (e.g., to prevent oxidation of) a stannous ion reducing agent. A "filler compound" also may be added to the solution to provide bulk or mass and to aid in the lyophilization process. Good results have been achieved using lactose as the filler compound.

An appropriate solvent is added to reconstitute the lyophilized preparation and the radionuclide is then added to initiate the radiolabeling reaction. Alternatively, an aqueous solution eluted off a radionuclide generator may be added directly to the lyophilized preparation.

A number of compounds are suitable for use as complexing agents. Examples of complexing agents that have been used to facilitate transfer of metals to proteins or strong chelating agents attached thereto include the polyhydroxycarboxylates, glucoheptonate, Burchiel et al., *J. Nucl. Med.* 27:896 (1986) and tartrate, Kasina et al., *Proc. Intl. Radio. Chem. Symp.* 269-271 (1986). Additional examples of complexing agents include, but are not limited to, gluconic acid, glucoheptonic acid, methylene diphosphonate, glyceric acid, glycolic acid, mannitol, oxalic acid, malonic acid, succinic acid, N,N'-bis(2-hydroxyethyl) ethylene diamine, citric acid, ascorbic acid and gentisic acid. Good results are obtained using gluconic acid or glucoheptonic acid as the complexing agent for $^{99m}$Tc, and citric acid as the complexing agent for $^{186}$ or $^{188}$Re.

In one embodiment of the invention, the complexing agent is a compound of the formula:

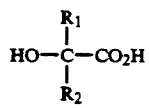

wherein $R_1$ and $R_2$ are independently selected from hydrogen or lower alkyl ($C_1$–$C_4$) groups. Alternatively, $R_1$ is hydrogen or a lower alkyl group ($C_1$–$C_4$) and $R_2$ is selected from —$CH_2$COOH, —$CH_2OH$, or —COOH. In another alternative, $R_1$ is OH and $R_2$ is —C(OH)$_2$COOH. Examples of some of the many complexing agents of this formula are malic acid, citramalic acid, 2-hydroxy-isobutyric acid, 2-ethyl-2-hydroxybutyric acid, glyceric acid, hydroxymalonic acid, 2,3-dihydroxy tartaric acid, and lactic acid. The structures of two complexing agents that have been used with good results are as follows:

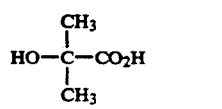

2-Hydroxyisobutyric Acid

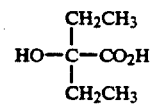

2-Ethyl-2-hydroxybutyric Acid

The radionuclide chelate compounds produced by using the above-described exchange complexes are used in the preparation of the conjugates of the present invention that comprise a radiolabled chelate compound attached to a bone targeting agent. The chelates produced using these exchange complexes also may be attached to other molecules to radiolabel the molecules.

For example, a chemically reactive moiety (a conjugation group) on a chelate may be reacted with a functional group on a targeting protien to bind the chelate thereto. See, for example, European Patent Application Publication No. 188,256. The targeting protein is a protein such as an antibody (preferably a monoclonal antibody) that binds to a desired target site within a human or mammalian host. The radiolabeled targeting proteins have diagnostic or therapeutic use, depending on the radionuclide in the chelate. An example of a target site is a tumor (cancer cells).

The present invention also provides a method for radiolabeing a chelating compound to form a radionuclide metal chelate. The method comprises reacting a radionuclide metal with a complexing agent to form an exchange complex, and contacting the exchange complex with a chelating compound under conditions such that the radionuclide metal is transferred from the exchange complex to the chelating compound, thereby forming said radionuclide metal chelate. The complexing agent is a compound of the formula:

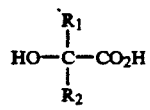

as described above. Preferably, the complexing agent is 2-hydroxyisobutyric acid or 2-ethyl-2-hydroxybutyric acid.

The chelating compound may be selected from any of the above-described chelating compounds comprising nitrogen and sulfur donor atoms. The radionuclide may be a radioisotope of technetium or rhenium, among others. The radionuclide metal may be reacted with the complexing agent in the presence of a reducing agent, and stabilizers and fillers also may be present. The chelating compound may be present in the reaction mixture during reaction of the radionuclide with the complexing agent. Alternatively, the chelating compound may be added after formation of the exchange complex, as described above.

The conditions under which the exchange complex is contacted with the chelating compound will vary according to such factors as the chemical structure of the particular complexing agent and chelating compound used. The reaction mixture containing the exchange complex and the chelating compound commonly is heated to promote transfer of the radionuclide, often to a temperature between 50° C. and 100° C. Other reaction conditions (e.g. pH) are chosen based on such factors as the conditions required for displacement of protecting groups from sulfer donor atoms.

Kits comprising a chelating compound and an exchange agent selected from 2-hydroxyisobutyric acid and 2-ethyl-2-hydroxybutyric acid also are provided by the present invention. The kits are useful for preparing radionuclide metal chelates in accordance with the above-described method.

Another aspect of the invention provides kits for producing radiolabeled compound-targeting agent conjugates for radiopharmaceutical use. Two types of diagnostic and therapeutic kits are prepared for use in the administration of chelate-targeting agent conjugates. The first type of kit ("pre-formed") comprises a compound to be radiolabeled and a targeting agent, each in separate containers. The compound is labeled with a radionuclide and then the resulting radiolabeled compound is joined to the targeting agent. Thus, the radionuclide is added to the compound prior to the addition of the targeting agent.

The second type of kit ("post-formed") comprises in one container a compound to be radiolabeled attached to a targeting agent and in another container one or more reagents for facilitating the radiolabeling, e.g., a reducing agent and a complexing agent which in combination are capable of allowing a metal, or metal oxide, radionuclide to form an exchange complex. Thus, the radionuclide is added to the compound after the addition of the targeting agent.

Preferred radionuclides for use in conjunction with a diagnostic kit include $^{99m}Tc$, $^{97}Ru$ and $^{203}Pb$ and with a therapeutic kit include $^{186}Re$, $^{188}Re$, $^{67}Cu$, $^{105}Rh$, $^{198}Au$, $^{199}Au$ and $^{212}Bi$. The discussion provided above regarding targeting agent is applicable here as well.

Yet another aspect of the invention provides methods for using the radiolabeled compound-targeting agent conjugates described above for diagnostic and therapeutic purposes. Targeting agents, such as those described above, direct the conjugates to calcified tissue.

Cancers and other disease states lead to increased pathological calcification. The targeting agents associate to a greater extent with those tissues undergoing increased calcification. Thus, abnormal calcified tissue, e.g., bone cancer, may be distinguishable from normal calcified tissue by increased levels of radioactivity delivered by a conjugate of the invention.

The diagnostic method of the invention may be used to detect the presence or absence of a calcified tissue target site, e.g., bone cancer, within a mammalian host. The method comprises the steps of administering to a mammal a diagnostically effective dose of one of the conjugates described above, where the conjugate is capable of associating with the target site. This step is followed by a step of detecting the biodistribution of the radionuclide in the mammal to determine the presence or absence of the target site in the host.

A diagnostically effective dose of a conjugate is generally from about 5 to about 35 and typically from about 10 to about 30 mCi per 70 kg body weight. The precise dose may depend upon the particular route of administration, e.g., intravenous, intracompartmental, intraarteoral or intratumoral. It will be evident to one skilled in the art how to determine the optimal effective dose for a particular chelate-targeting agent conjugate and a particular route of administration. The discussion provided above regarding targeting agent is applicable here as well. Preferred radionuclides include $^{97}Ru$, $^{99m}Tc$ and $^{203}Pb$. A preferred mammal is man.

The therapeutic method may be used for delivering a radionuclide to a calcified tissue target site, e.g., bone cancer, within a mammalian host. The method comprises the step of administering to a mammal a therapeutically effective dose of one of the conjugates described above, where the conjugate is capable of associating with the target site. A therapeutically effective dose is generally from about 20 mCi to about 300 mCi. The discussion immediately above regarding the precise dose of a radiolabeled compound-targeting agent conjugate applies here as well. Preferred radionuclides include $^{186}Re$, $^{188}Re$, $^{67}Cu$, $^{105}Rh$, $^{198}Au$, $^{199}Au$ and $^{212}Bi$. A preferred mammal is man.

To summarize the examples which follow, Example I describes the conjugation of a diphosphonate to a chelating compound. Example II describes the incorporation of a diphosphonate during synthesis of a chelating compoud. Example III provides the preparation of a radiolabeled chelate and its conjugation with a bone seeking agent. Example IV provides the preparation of a bone seeking agent-chelating compound conjugate, followed by labeling with $^{99m}Tc$ or $^{186/188}Re$. Example V describes biodistribution studies in mice.

The following examples are offered by way of illustration and not by way of limitation.

EXAMPLES

Example I

Conjugation of Diphosphonate to Chelating Compound

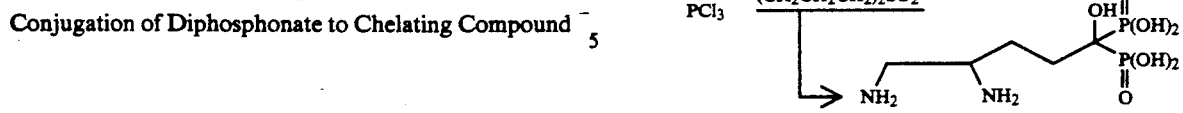

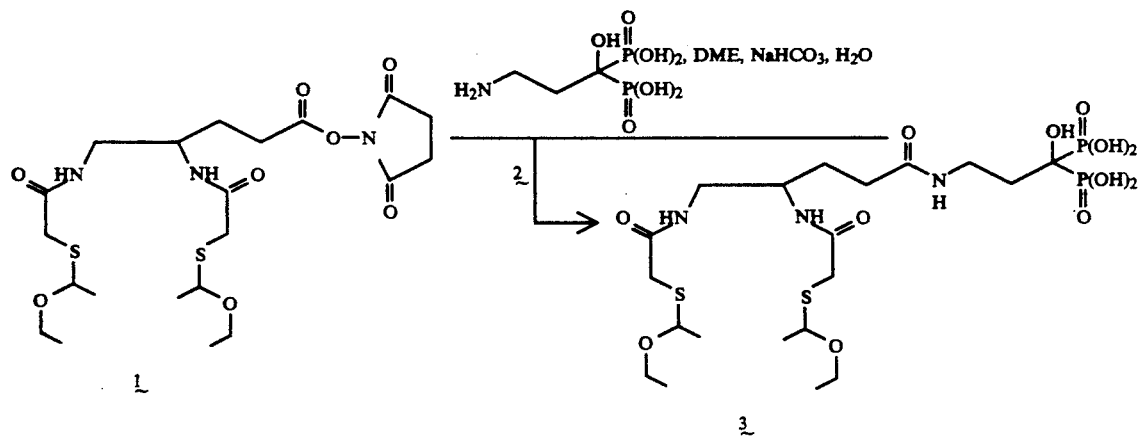

A solution of 3-amino-1-hydroxypropane-1,1-diphosphonic acid (2) and 4.0 equivalents of sodium hydrogen carbonate in water is stirred while a solution of 1 in 1,2-dimethoxyethane is added dropwise over a period of 0.5 hours. The mixture is then stirred at room temperature for 2.0. The solvent is removed in vacuo and the resulting residue is eluted through a column of DEAE sephadex using aqueous triethylammonium bicarbonate. The product containing fractions are combined and concentrated to a residue. The final product is isolated as a sodium salt by precipitation from acetone with sodium perchlorate.

Example II

Incorporation of Diphosphonate During Synthesis of Chelating Compound

A. Synthesis of 4,5-Diamino-1-Hydroxypentane-1,1-Diphosphonic Acid

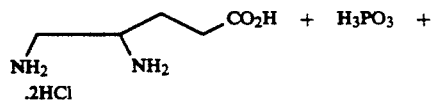

A mixture of 4,5-diaminopentanoic acid dihydrochloride and phosphorous acid (2.7 equivalents) in n-propyl sulfone is heated at 100° C. while 2.1 equivalents of phosphorous trichloride is added dropwise. The reaction mixture is heated for three hours, then 25 ml of water is added and the heating continued for 1.5 hours. The solution is filtered and transferred to a separating funnel. The aqueous layer is transferred to a flask and 20 mls of methanol is added dropwise and the mixture is refluxed overnight. The mixture is then cooled to give a precipitate. The solution is decanted off and 10 ml of H₂O is added to the gummy precipitate and the mixture is then heated to reflux for 1.5 hours. The mixture is cooled to give a precipitate which is collected by filtration ad washed with cold methanol/water then washed with ether. The final product is then air dried.

B. Synthesis of N₂S₂ Ligand Diphosphonic Acid 1

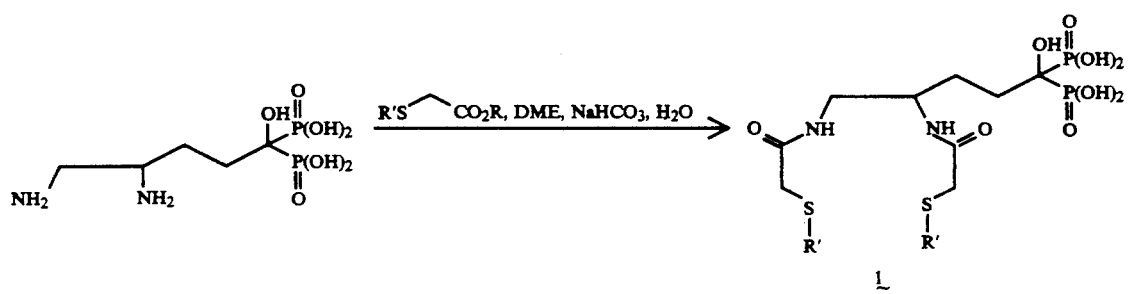

R = active ester e.g. 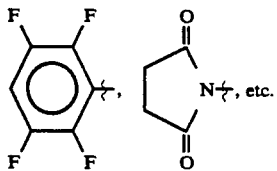

R' = sulfur protective group, e.g. 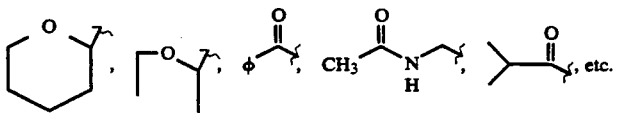

The N₂S₂ ligand diphosphonic acid is prepared in a manner similar to that described in *Reactivity and Structure Concepts in Organic Chemistry*, Volume 21, "The Practice of Peptide Synthesis," M. Bodenszky, p.138, Springer-Verlag (1984):

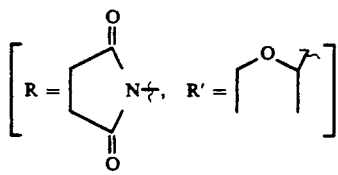

A solution of 4,5-diamino-1-hydroxypentane-1,1-diphosphonic acid and 4.0 equivalents of sodium hydrogen carbonate in water is stirred while a solution of S-(1-ethoxy)ethylmercaptoacetic acid succinimidyl ester (2.5 equivalents) in 1,2-dimethoxyethane is added dropwise over a period of 0.5 hours. The mixture is then stirred at room temperature for an additional 3.0 hours. The solvents is removed in vacuo and the resulting residue is eluted through a column of DEAE sephadex using aqueous triethylammonium bicarbonate. The product containing fractions are combined and concentrated to a residue. The product is isolated by dissolving the residue in acetone and precipitating the material as the sodium salt by addition of a solution of sodium perchlorate in acetone.

Example III

Preparation of Radiolabeled Chelate and Conjugation with Bone Seeking Agent

A. Radiolabeling of Chelating Compounds

1. Technetium-99m labeling

Method a: To 100 μl of solution containing 5 mg of sodium gluconate and 0.1 mg of SnCl₂ in water, at pH=6.1, 75-100 mCi of 1 mL. $^{99m}TcO_4$ (pertechnetate) is added. After incubation at room temperature for 10 min. to form a $^{99m}$Tc-gluconate complex, 100 μg of a chelating compound dissolved in i-propanol:acetic acid, 90:10, at 1 mg/mL, 80 μl of 0.2N HCl and 200 μL of i-propanol are added in that order. The reaction mixture is heated to 75° C. for 15 min., then cooled in ice for 5 min.

Method b: Alternatively, 1.0 mL of $^{99}Mo/^{99m}Tc$ generator eluted pertechnetate (75-100 mCi) is added to a vial containing a lyophilized mixture comprising sodium gluconate, stannous chloride, 0.1 mg; gentisic acid, 0.1 mg; lactose, 25 mg at pH 6.1. The vial is agitated gently to mix the contents by inversion and then incubated at room temperature for 10 min.

2. Rhenium-188 labeling

The $^{188}$Re chelate of the chelating compound is prepared by a similar procedure. Sodium perrhenate (3 mL, 30 mCi/mL produced from a $^{188}W/^{188}Re$ generator) is added to a vial containing a lyophilized mixture comprising citric acid, 75 mg; stannous chloride, 0.75 mg; gentisic acid, 0.25 mg and lactose, 100 mg. The vial is agitated gently to mix the contents, then incubated at room temperature for 10 min. To a separate vial containing 0.50 mg of the chelating compound, 0.50 mL of 2-propanol is added and the vial is agitated for 2 min. to completely dissolve the compound. Then 0.3 mL of this solution is transferred to the vial containing the $^{188}$Re-citrate complex. The reaction mixture is heated to 75° C. for 15 min., then cooled in ice for 5 min.

3. Rhenium-186 labeling

The $^{186}$Re chelate of the chelating compound is prepared by a procedure similar to the $^{188}$Re procedure. Perrhenate $^{186}ReO_4$ as sodium, lithium, ammonium or any other suitable counter ion is obtained from irradiation of $^{185}$Re (0.1 to few mg) in a nuclear reactor dissolution and purification of the original solution by previously described procedure (Venderhyden et al., *Inorg. Chem.* 24:1666, 1985) or any other suitable procedure. To the $^{186}ReO_4$ vial is added 0.75 mL reconstituted solution made of 1.0 mL of sterile water added to a vial containing a lyophilized mixture comprising citric acid 25 mg, stannous chloride 1 mg, gentisic acid 1 mg and lactose 75 mg.

The vial is agitated gently to mix the contents, then incubated at room temperature of 75° C. To the separate vial containing the chelating compound, 2-propanol is added to obtain a completely dissolved solution. An appropriate amount of this solution to give a ligand to rhenium mole ratio of 1:5 (preferentially between 1 and 1.5 ligand to rhenium mole ratio) is then transfered to the vial containing the $^{186}$Re-citrate complex. The reaction mixture is heated to 75° C. for 20 min. then cooled on ice for 5 min.

B. Conjugation of Radiolabeled Chelate with Bone Seeking Agent

To the above $^{99m}$Tc chelate, 100 μl of bicarbonate buffer is added so that the pH of the solution is about 6.0. Next, 100-500 μl of a solution containing a bone seeking agent at 0.1 to 10 mg/mL is added in the same buffer to reach a final pH of 8 to 9.5. The reaction mixtures are incubated at room temperature for 5-30 min. as necessary. The ITLC procedure (*Nuclear Medicine Technology and Techniques*, ed. Bernier, D., Longan, J., and Wells, L.: The C. V. Mosby Co., St Louis, Mo., 1981; pp. 172-174) using 100% CH$_3$CN is utilized to determine the percentage of the conjugate.

If necessary, an extra purification step is added to increase the purity of the conjugate. This involves passing the conjugate through an ion exchange (DEAE, CAC, Sephadex, ACCEL®) or the like) or reverse phase column. The conjugate is either collected in the flow through or eluted with solution of appropriate ionic strength.

Example IV

Preparation of Bone Seeking Agent-Chelating Compound Conjugate Followed by Labeling with $^{99m}$Tc or $^{188}$Re

A. Preparation of the Conjugate

The antibody conjugation reaction is performed in a final volume of 4.0 mL: 1 mg of a chelating compound (61.67 μmol), 1.1 mg of a bone seeking agent, 1-2 mL of distilled dimethyl formamide (if necessary to solubilize the chelating compound), 0.05M of borate or 0.5M bicarbonate buffer at pH 8.5. After stirring for 90 min. at room temperature, 4.4 mL of 5N sodium chloride is added. After an additional 30 min., the reaction mixture is centrifuged to remove any particulates. The supernatent is fractioned by gel filtration column chromatography and concentrated.

B. Radiolabeling of the Conjugate

1. Technetium-99m labeling

Method a: Stannous gluconate kits are prepared containing 5 μg sodium gluconate, 100 μg stannous chloride, 100 μg of chelating bone seeking ligand and 25 μg of lactose. The pH is contained between 2 and 7 using HCl, Acetic acid or NaOH. To the stannous gluconate kit is added 1.0 uL sodium pertechnetate (Tc-99m) about 50 mCi. The vial is heated at 75°-100° C. for 5-15 min. The percent formation of the conjugate, remaining TcO$_4$ and hydrolyzed reduced technetium is determined by ITLC SG using 100% CH$_3$CN and HPLC reverse phase using a C$_{18}$ column and a mobile phase ranging between 0 and 40% Acetonitrile/phosphate buffer. The technetium incorporation typically ranges from 75% to 99% on a chelating bone seeking conjugate.

Method b: To 100 μl of chelating bone seeking ligand (1 mg/ml) is added 100 μL of 1N NaOH and 1.0 ml of sodium pertechnetate (50 mCi). Extemporaneously a stock solution of sodium dithionite is prepared by addition of 5 uL water to a vial containing 250 ug of sodium dithionite: a 100 μL aliquot is removed and quickly added to the pertechnetate liquid vial. The reaction vial is heated at 75°-60° C. for 5-15 min. After a few minutes cooling at room temperature, 100 μl of 1N HCl and 0.3 uL of 0.2M sodium phosphate pH 7.4 are added. The percent formation of the conjugate, remaining TcO$_4$ and hydrolyzed reduced technetium is determined by ITLC SG using 100% CH$_3$CN and HPLC reverse phase using a C$_{18}$ column and a mobile phase ranging between 0 and 40% Acetonitrile/phosphate buffer. The technetium incorporation typically ranges from 75% to 99% on a chelating bone seeking conjugate.

Method c: Stannous tartrate kits are prepared in an evacuator vial under nitrogen to contain 0.5 mL of disodium tartrate (10 mg/ml) and 0.1 mL stannous chloride (1.0 mg/ml in ethanol). The pH of the solution is kept between 4 and 7, perferably 6.0. To this stannous solution is added 0.5 mL of sodium pertechnetate (Tc-99m) (15 mCi) and the preparation isallowed to stand at room temperature. In an evacuated vial, 200 uL of sodium phosphate (0.2M, pH 8 or 10) and 200 uL of chelating-bone seeking ligand (0.1-5 mg/mL) are added successively. Then 250 uL of $^{99m}$Tc-tartrate (3-5 mCi) is added and the vial is heated for 5-60 min. at 37°-100° C., preferably 60 min. at 75° C. The percent formation of the conjugate, remaining TcO$_4$ and hydrolyzed reduced technetium is determined by ITLC SG using 100% CH$_3$CN and HPLC reverse phase using a C$_{18}$ column and a mobile phase ranging between 0 and 40% Acetonitrile/phosphate buffer. The technetium incorporation typically ranges from 75% to 99% on a chelating bone seeking conjugate.

2. Rhenium-188 labeling

Method a: Sodium perrhenate (3 mL, 15 mCi, produced from a $^{188}$W/$^{188}$Re generator) is added to a vial containing a lyophilized mixture comprising: citric acid, 75 mg; stannous chloride 0.75 mg; gentisic acid 3 mg; lactose 75 mg and 0.1-1 mg of the chelating bone seeking ligand. The pH is contained between 1.5 and 7 using HCL, acetic acid or NaOH. The vial is heated at 75°-100° C. for 5-15 minutes. The pH is then adjusted to 7-7.4. The percent formation of the conjugate, remaining rhenium oxide and hydrolyzed reduced rhenium is determined by ITLC SG using 100% CH$_3$CN and HPLC reverse phase using a C$_{18}$ column and a mobile phase ranging between 0 and 40% acetonitrile/phosphate buffer. The rhenium incorporation typically ranges from 75% to 99% on a chelating bone seeking conjugate.

Method b: Sodium perrhenate (3 mL, 15 mCi, produced from a $^{188}$W$^{188}$Re generator) is added to a vial containing a lyophilized mixture comprising a hydroxy isobutyric acid 50-300 mg; stannous chloride 0.5-5 mg; gentisic acid 0.25-5 mg; lactose 75 mg and 0.1-1 mg of the chelating bone seeking ligand. The pH is contained between 1.5 and 7 using HCL, acetic acid or NaOH. The vial is incubated at room temperature for 5-60 min. or heated at 75°-100° for 5-15 min. After a few minutes cooling if necessary, the pH is raised to 8-9.5 using a sufficient amount of a carbonate buffer or NaOH. The vial is incubated again at room temperature for 5-60 min. The pH is then adjusted to 7-7.4. The percent formation of the conjugate, remaining rhenium oxide and hydrolyzed reduced rhenium is determined by ITLC SG using 100% CH$_3$CN and HPLC reverse phase using a C$_{18}$ column and a mobile phase ranging between 0 and 40% acetonitrile/phosphate buffer. The rhenium incorporation typically ranges from 75% to 99% on a chelating bone seeking conjugate.

3. Rhenium-186 labeling

Method a: The $^{186}$Re chelate form of the conjugate is obtained by a procedure similar to the $^{186}$Re labeling of the chelating compound described above. To the purified perrhenate vial is added 0.75 mL of the reconstituted solution made of 1.0 mL of sterile water added to a vial containing a lyophilized mixture comprising citric acid 25 mg, stannous chloride 1 mg, gentisic acid 1 mg, lactose 75 mg and 0.1-10 mg of the chelating bone seeking ligand. The vial is incubated at 75° C. for 15-30 min., then cooled at room temperature. The pH is then adjusted to 7.0-7.4. The percent formation of the conjugate, remaining rhenium oxide and hydrolyzed reduced rhenium is determined by ITLC SG using 100%

CH₃CN and HPLC reverse phase using a C₁₈ column and a mobile phase ranging between 0 and 40% acetonitrile/phosphate buffer. The rhenium incorporation typically ranges from 75% to 99% on a chelating bone seeking conjugate.

Method b: Sodium perrhenate (3 mL, 15 mCi, produced from a $^{188}W^{188}Re$ generator) is added to a vial containing a lyophilized mixture comprising a hydroxy isobutyric acid 50-300 mg; stannous chloride 0.5-5 mg; gentisic acid 0.25-5 mg; lactose 75 mg and 0.1-10 mg of the chelating bone seeking ligand. The pH is contained between 1.5 and 7 using HCL, acetic acid or NaOH. The vial is incubated at room temperature for 5-60 min. or heated at 75°-100° for 5-15 min. After a few minutes cooling if necessary, the pH is raised to 8-9.5 using a sufficient amount of a carbonate buffer or NaOH. The vial is incubated again at room temperature for 5-60 min. The pH is then adjusted to 7-7.4. The percent formation of the conjugate, remaining rhenium oxide and hydrolyzed reduced rhenium is determined by ITLC SG using 100% CH₃CN and HPLC reverse phase using a C₁₈ column and a mobile phase ranging between 0 and 40% acetonitrile/phosphate buffer. The rhenium incorporation typically ranges from 75% to 99% on a chelating bone seeking conjugate.

Example V

Biodistribution Studies in Mice

Conjugates are injected into Balb/c mice. The biodistribution of the conjugate is analyzed for 2 hours after injection according to the method of Hwang et al., Cancer Res., 45: 4150-4155 (1985). The data is collected in terms of the percentage of the injected radioactivity per gram (% inj. dose/gram) of each specified tissue type and bone/tissue ratio of injected radioactivity. The tissue types evaluated are as follows: blood (BL); tail (TA); tumor (TU); skin (SK); muscle (MU); bone (BO); lung (LU); liver (LI); spleen (SP); stomach (ST); thyroid (TH); kidney (KI); and intestine (IN). FIGS. 1 and 2 compare $^{99m}Tc$-labeled phosphonates, e.g., "MDP" and "ADP-KIT," with representative conjugates.

Example VI

Preparation of Radiolabeled Chelate Compounds and Attachment Thereof to Targeting Agents The compounds 2-hydroxy-isobutyric acid and 2-ethyl-2-hydroxy butyric acid were used as complexing agents in the radiolabeling of an N₃S chelating compound having the following structure:

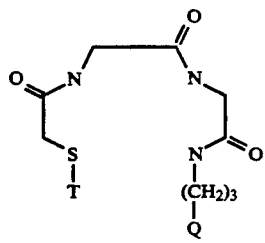

wherein T represents a sulfur protecting group and Q represents a conjugation group. One such compound comprises a hemithioacetal sulfur protecting group such as an ethoxyethyl group of the formula:

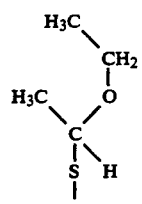

wherein the sulfur atom is the sulfur donor atom of the chelating compound. One example of a suitable conjugation group Q is an ester group such as a tetrafluorophenyl ester of the formula:

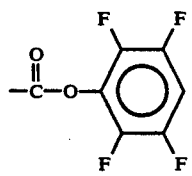

The chelating compound was radiolabeled with $^{99m}Tc$ by combining the following reagents (solvents were purged with nitrogen):

lactose (20 mg);
2-ethyl-2-hydroxybutyric acid (5 mg, 1 mg/mL in saline);
gentisic acid (100 ug in 0.1 mL saline);
sodium pertechnetate (100 ul eluent, about 100 mCi, from a $^{99}Mo/^{99}Tc$ generator, generators are commercially available from DuPont, Mediphysics, E. R. Squibb, or Mallinckrodt);
SnCl₂ (100 ug in 0.1 mL ethanol, dried with N₂ prior to the addition of the reagents); and
chelating compound (100 ug, 1 mg/mL in isopropyl alchohol).

The reaction vial was shaken and heated for ten minutes at 75° C. Since the ethoxyethyl sulfur protecting group is displaced by metal assisted acid cleavage during radiolabeling, the radiolabeling reaction was conducted at acidic pH, preferably about 2.2-2.5 for this chelating compound. Analysis by HPLC showed 81% ester and ITLC showed 1.1% TcO₂. The radiolabeled chelate compound may be purified using any suitable chromatography column. Good results were achieved using a pD10 column.

In another radiolabeling reaction, 1 mL of diluted $^{99}Mo/^{99}Tc$ generator eluent (about 75-100 mCi) and 100-300 ul isopropyl alcohol were added to a lyophilized preparation comprising:

lactose (20 mg);
2-ethyl-2-hydroxybutyric acid (5 mg);
chelating compound (50 ug);
gentisic acid (100 ug); and
SnCl₂ (100 ug).

The reaction vial was immediately placed in a boiling water bath at 95°-100° C. Aliquots were taken at 1, 3, 5, 10 and 15 minutes. The pH of the reaction mixture was 2.77.

The ester yields as a function of the time points listed above are 76%, 88%, 68%, 60% and 45% respectively.

The corresponding TcO₂ values are 5.2%, 3.4%, 3% and 4% (ITLC as thioglycolates).

From the above data, the optimal time at 100° C. is three minutes. The ester yield was 88%. The heating for longer periods decreases the yield. The TcO$_2$ values are very good at all time points.

2-Hydroxyisobutyric acid may be substituted for 2-ethyl-2-hydroxybutyric acid as the complexing agent in the above radiolabeling reactions. Other chelating compounds may be used as well. In alternative radiolabeling reactions, the components other than the chelating compound are incubated for 10 minutes at room temperature to form the exchange complex. The chelating compound then is added, and the reaction mixture is heated to 75°-100° C. to form the chelates.

The $^{99m}$Tc-labeled chelate produced by the above radiolabeling procedures is attached to a targeting agent. A conjugation moiety on the chelate (e.g., the tetrafluorophenyl ester group, which survives the radiolabeling procedures conducted at acidic pH) is reacted with a functional group on the desired targeting agent to bind the chelate thereto.

Reactions for attaching chelates to bone-targeting agents are described above. Alternatively, the chelate may be reacted with a targeting protein such as an antibody in a buffered solution at a pH of about 9-11. The ester conjugation group will react with free amine groups on lysine residues of the protein.

From the foregoing, it will be appreciated that, although specific embodiments of the invention have been described herein for purposes of illustration, various modifications may be made without deviating form the spirit and scope of the invention.

We claim:

1. A conjugate of a radiolabeled compound and a targeting agent that is capable of associating with calcified tissue, wherein said targeting agent is a phosphorus-containing compound which contains a C—O—P bond, a P—O—P bond, a C—C—P bond, a P—C—P bond, a P—N—P bond or combinations thereof, and wherein said radiolabled compound comprises the formula:

*X—Ar—R wherein
*X is a radioisotope of iodine, bromine, fluorine, or astatine;
Ar is aromatic or heteroaromatic ring;
R is a chemical bond or a substituent containing 1 to 12 straight-chain carbon atoms that does not activate Ar toward electrophilic substitution on the order produced by hydroxy or amino substitution of the ring, wherein said bond or said substituent has attached thereto a functional group suitable for conjugation.

2. The conjugate of claim 1 wherein *X is $^{123}$I, $^{125}$I, $^{131}$I, $^{75}$Br, $^{76}$Br, $^{77}$Br, $^{18}$F, or $^{211}$At.

3. The conjugate of claim 1 wherein the calcified tissue is bone.

4. A method of detecting the presence or absence of a calcified tissue target site within a mammalian host, comprising the steps of:
administering to a mammal a diagnostically effective dose of the conjugate of claim 1 wherein the conjugate is capable of associating with said target site; and
detecting the biodistribution of said conjugate in said mammal to determine the presence or absence of said target site in said host.

5. The method of claim 4 wherein the calcified tissue target site is bone cancer.

* * * * *

UNITED STATES PATENT AND TRADEMARK OFFICE
CERTIFICATE OF CORRECTION

PATENT NO. : 5,202,109
DATED : April 13, 1993
INVENTOR(S) : Alan R. Fritzberg et al.

It is certified that error appears in the above-identified patent and that said Letters Patent is hereby corrected as shown below:

On the title page, item [21], please delete "643,578" and substitute therefor -- 648,578 --.

In column 30, claim one, line three, please delete "radiolabled" and substitute therefor -- radiolabeled --.

Signed and Sealed this

Fourteenth Day of December, 1993

Attest:

BRUCE LEHMAN

Attesting Officer          Commissioner of Patents and Trademarks